US00PP28730P2

(12) United States Plant Patent
Hansen

(10) Patent No.: US PP28,730 P2
(45) Date of Patent: Dec. 5, 2017

(54) ***HIBISCUS* PLANT NAMED 'SUMMER IN PARADISE'**

(50) Latin Name: ***Hibiscus* hybrid (L.)**
Varietal Denomination: Summer in Paradise

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/530,318

(22) Filed: Dec. 21, 2016

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell

(57) ABSTRACT

A new and distinct cultivar of winter-hardy, herbaceous, perennial, hybrid *Hibiscus* plant named 'Summer in Paradise' comprising a upright habit of multiple, well-branched, basal stems producing flowers from the top to bottom of the plant. Flowers are hot cerise red with dark red shiny eye accented with a column producing bright yellow pollen. The foliage is three to five-lobed, deeply incised, and dark green colored blushed with greyed reddish-purple.

1 Drawing Sheet

Botanical classification: *Hibiscus* hybrid (L.).
Variety denomination: 'Summer in Paradise'.

BACKGROUND AND ORIGIN OF THE PLANT

The present invention relates to the new and distinct hardy, herbaceous, *hibiscus* plant, *Hibiscus* 'Summer in Paradise' hybridized under direction of the inventor on Jul. 23, 2012 at a wholesale perennial nursery in Zeeland, Mich. The new plant is a single seedling selected from a cross between a proprietary unreleased rose mallow known by the breeder code 11-42 times 'Jazzberry Jam' (not patented). The seeds were harvested in the fall of 2012 and the specific seedling which passed the initial trial in the summer of 2014 at which time it was assigned the breeder code labeled # 12-135-2. Both parents have a complex mixture of species in them, comprising the species: *moscheutos* and *coccineus*. *Hibiscus* 'Summer in Paradise' was first asexually propagated in 2014 by sterile shoot-tip tissue culture at the same nursery in Zeeland, Mich. The resultant asexually propagated plants have been found to be stable and true to type in successive generations of asexual reproduction.

No plants of *Hibiscus* 'Summer in Paradise' have been sold under this or any name, either in this country or anywhere in the world, prior to the filing of this application, nor has any disclosure been made prior to the filing of this application with the exception of that which was within one year of the filing of this application and was derived directly or indirectly from the inventor.

BRIEF SUMMARY OF THE PLANT

*Hibiscus* 'Summer in Paradise' differs from its parents as well as all other hardy herbaceous *hibiscus* known to the applicant in many traits. The most similar *hibiscus* in flower color known to the applicant are *Hibiscus* 'Sultry Kiss' U.S. Plant Pat. No. 23,300, 'Cranberry Crush' U.S. Plant Pat. No. 21,984, 'Mars Madness' U.S. Plant Pat. No. 27,838 and 'Vintage Wine' U.S. Plant Pat. No. 27,839. The new plant differs from 'Sultry Kiss' most significantly in having a more compact habit and more basal branching. Compared with the new plant, 'Cranberry Crush' has flower petals are more cupped, the petal color has a more reddish orange hue and less reddish purple and the plant habit is shorter and less broad. Compared with 'Mars Madness' the new plant is more upright in habit with larger flowers of a slightly different color and the foliage is more frequently five-lobed. The new plant compares with 'Vintage Wine' by having a more frequently five-lobed leaf rather than ovate of 'Vintage Wine' and the flower is larger and less reddish-purple hue. Compared with 'Jazzberry Jam' the new plant is more compact in habit, has flatter less ruffled petals and the flower is more hot cerise red rather than the pinkish-magenta. Comparison of the female parent is not possible as the parent was not maintained.

*Hibiscus* 'Summer in Paradise' is a unique hardy herbaceous *hibiscus* with the following combined traits:

1. Winter-hardy, perennial with upright habit of multiple, well-branched, basal stems.
2. Many rotate flowers of hot cerise red produced from bottom to top of plant.
3. Flower petals having darker red eye zone set off with column of bright yellow pollen.
4. Dark green, deeply-incised, tri- to penta-lobed foliage blushed with greyed reddish-purple.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
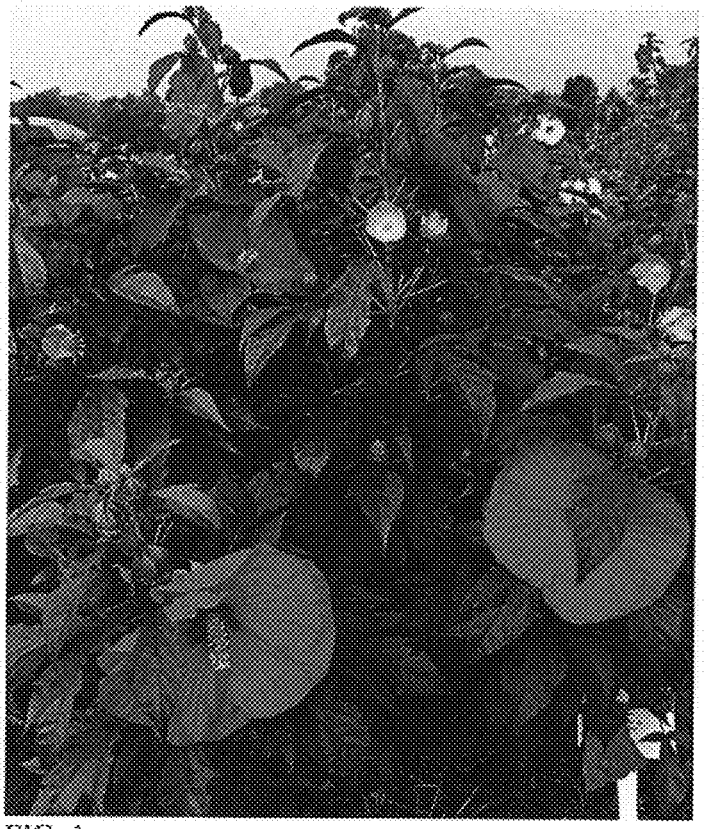
FIG. 1 shows a four-year-old plant in full flower in a trial garden.
Figure 2:
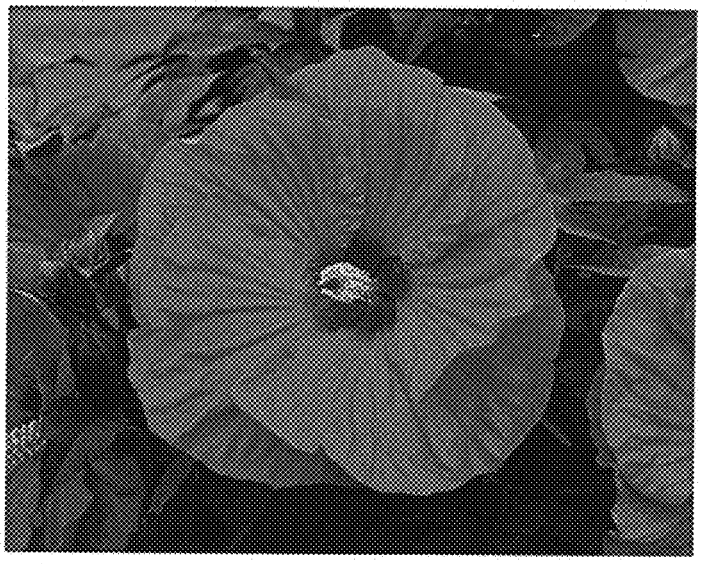
FIG. 2 shows a close-up of the flower.

The following descriptions and color references are based on the 2001 edition of The Royal Horticultural Society Colour Chart except where common dictionary terms are used. The new plant, *Hibiscus* 'Summer in Paradise', has not been observed under all possible environments. The phenotype may vary slightly with different environmental conditions, such as temperature, light, fertility, moisture and maturity levels, but without any change in the genotype. The following observations and size descriptions are of three-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: A proprietary unreleased *hibiscus* known by the breeder code 11-42 (female, seed parent) with 'Summer Storm' U.S. Plant Pat. No. 20,443, 'Plum Crazy' U.S. Plant Pat. No. 11,854 and 'Midnight Marvel' U.S. Plant Pat. No. 24,079 in the background times *Hibiscus* 'Jazzberry Jam' (male, pollen parent).

Propagation:

*Method*.—Stem cuttings and sterile shoot-tip plant tissue culture division.

*Time to initiate roots from tissue culture*.—About two weeks.

*Rooting habit*.—Normal, branching, developing thick to about 2.8 cm diameter, fleshy; root color creamy yellow between RHS 161D and lighter than RHS 159D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about 26 thick upright and heavily branched main stems producing an upright spreading mound to about 175.0 cm tall and about 150.0 cm wide; about 8 primary branches per main stem protruding at about 45° from horizontal; flowering from base to top of plant with up to about 54 flowers per main stem, average flowers per stem about 38.

*Stem*.—Terete, glabrous, glaucous; to about 175.0 cm tall and about 2.8 cm diameter at base, average about 160.0 cm tall and about 24.0 mm diameter at base.

*Stem color*.—Between RHS 144B and RHS 144A blushed with nearest RHS 187A in regions of high light exposure.

*Lateral branches*.—Average about 8 per stem; terete, glabrous, glaucous; to about 43.0 cm long and 8.0 mm diameter, smaller distally.

*Lateral branch color*.—Between RHS 144B and RHS 144A blushed with nearest RHS 187A in regions of high light exposure.

*Internode*.—About 24 nodes per stem below flowers, average internode length about 4.0 cm of unpinched plant below flowers.

*Internode color*.—Same as surrounding stem.

Foliage description: Alternate; coarsely and irregularly dentate; apex and side lobes acute; base rounded; glabrous abaxial and adaxial; deeply incised nearly to petiole, tri- to penta-lobed; slightly lustrous adaxial surface, matte abaxial surface; leaf blades to about 22.0 cm long and about 25.0 cm across, average blade size 18.0 cm long and 16.0 cm wide; no fragrance detected.

*Foliage color*.—Young expanding leaves — adaxial nearest RHS 137 A with blush of nearest RHS N187A, abaxial nearest RHS 144A with blushing of nearest RHS N187A; distal mature leaves — adaxial nearest RHS 139A, abaxial nearest RHS 147B; proximal mature leaves — adaxial between RHS 139A and RHS 137A, abaxial between RHS 138A and RHS 146A.

*Veins*.—Palmate; lustrous; costate on abaxial.

*Vein color*.—Young abaxial nearest RHS 147C and adaxial nearest RHS 187C; mature abaxial nearest RHS 145C with some blushing of nearest RHS 187C and adaxial between RHS 187C and RHS 187B.

*Petioles*.—Mostly terete, proximally slightly applanate on adaxial side near base; glaucous; glabrous; to about 14.5 cm long and 7.5 mm diameter at base, average size about 10.0 cm long and 6.2 mm wide at base.

*Petiole color*.—On young expanding leaves adaxial nearest RHS 146D with tinting of nearest RHS 187A, abaxial base nearest RHS 144A with blush of nearest RHS 187A; on mature leaves adaxial nearest RHS 146D blushed with nearest RHS 183B, abaxial nearest RHS 144A.

Flower description: Complete; actinomophic; mostly outward facing; rotate; lasting up to two days on plant; no fragrance detected.

*Buds one day prior to opening*.—Ellipsoid with rounded apex and bluntly rounded base; sepals adpressed to petals, carinate at sepal fusions; about 8.2 cm long and about 5.6 cm diameter at petal base; petals opening slightly distally one to two days prior to flattening.

*Bud color*.—Exposed petal color between RHS 187C and RHS 60A with lighter veins the same color.

*Epicalyx*.—Typically 11 per flower; linear; entire, glabrous, with margin micro ciliate; dull surface abaxial and adaxial; sharply acute apex and truncate base, arcuate upwards near apex; about 2.9 cm long and base of about 4.0 mm wide.

*Epicalyx color*.—Adaxial between RHS 138A and RHS 146A, abaxial nearest RHS 146A.

*Sepals*.—Five, fused in basal 1.8 cm to form star-shaped hypanthium about 8.2 cm across and 2.0 cm deep; acute apex; glabrous; margin entire, edentate; abaxial and adaxial surfaces matte; about 4.2 cm long, about 3.0 cm wide at fusion.

*Sepal color*.—Adaxial base nearest RHS 146C and distal nearest RHS 146B, veins nearest RHS 145B; abaxial between RHS 144A and RHS 146B, veins not apparent, same as surrounding tissue.

*Flowers*.—Solitary, up to 54 per main stem without pinching; slightly cupped petals; mostly outwardly facing; natural spread to about 25.0 cm across and 8.0 cm deep from center to edge of petals; smaller in later season; with lustrous red eye about 4.8 cm across; persist for one to two days; effective for at least 7 weeks beginning early August; no detectable fragrance.

*Petals*.—Five; microscopically puberulent abaxial and adaxial, glabrous eye; adnate to the androecium to form a column, imbricate to about 100% overlapping at widest part (petals overlapping completely to the petals on either side); petal near leading (inside) with slight longitudinal fold; palmately veined, primary and secondary veins impressed on adaxial and costate abaxial; shape: rounded with distinct claw and limb; margins: entire, edentate; apex: rounded; base: short claw-like; size: average about 17.3 cm across and about 12.5 cm long, claw base about 12.5 mm across (larger in earlier part of flowering season).

*Petal color*.—Adaxial nearest RHS 61B with eye nearest RHS 53A, and veins in longitudinal center near RHS 53A; abaxial basal 1.5 cm between RHS 61D and RHS 61C, mid-section to perimeter between RHS 61B and RHS 60C with veins between RHS 53B and RH 53C.

*Gynoecium*.—Single; partially enclosed in column. Column: glabrous except base micro-puberulent, lustrous; about 5.2 cm long and base about 12.0 mm across; with pistil protruding about 12.0 mm. Column color: between RHS 60A and RHS 46A in basal 0.5 cm, middle portion nearest RHS 59D and distal end between RHS 60A and RHS 46A. Style: micro-puberulent in region above column; about 6.3 cm long, penta-furcate in about distal 9.0 mm; branch diameter about 1.2 mm; color nearest RHS 53A. Stigma: typically five; flattened globose, puberulent, about 4.5 mm in diameter and 1.5 mm tall; color nearest RHS 53A. Ovary: superior, semi-globose, rounded apex and flat base; about 10.0 mm across at base and about 7.0 mm tall; acute apex; color between RHS 145B and RHS 145C.

*Androecium*.—Filaments: numerous, about 100; about 7.0 mm long and about 0.3 mm diameter; attached along nearly the entire length of column; color nearest RHS 60C proximally and nearest RHS 60D distally. Anthers: flattened ellipsoid; dorsifixed; about 2.5 mm long and 2.0 mm across and about 0.8 mm thick; color nearest RHS 8B. Pollen: abundant, globose, less than 0.1mm long; color nearest RHS 8A.

Pedicel: Terete, glabrous, glaucous; length from base of sepal to abscission point about 9.0 cm long, from abscission point to stem node about 6.6 cm long; about 3.5 mm wide; longer on early flowers and decreasing in distal flowers; color nearest RHS 146B above abscission and below nearest RHS 146D.

Peduncle: Terete, glabrous, glaucous; flowering in the distal 56.0 cm; color nearest RHS 146C.

Fruit: Penta-loculicidal capsule; pubescent along inner septa, glabrous outside; nearly globose, cuspidate apex and flattened base; about 30.0 mm long and 30.0 mm diameter; color nearest RHS 200B when mature.

Seed: Minutely floccose; globose; about 4.5 mm in diameter; color nearest RHS N200A.

Resistance: *Hibiscus* 'Summer in Paradise' has not displayed any pest and disease resistance beyond that typical of hardy perennial *hibiscus*. The plant grows best with plenty of moisture, but is able to tolerate some drought once established. Hardiness at least from USDA zone 4 through 9, and other disease resistance is typical of that of other hardy *hibiscus* cultivars.

I claim:

1. A new cultivar of hardy herbaceous perennial *Hibiscus* hybrid plant named 'Summer in Paradise' as herein illustrated and described.

* * * * *